United States Patent [19]

Socci et al.

[11] Patent Number: 5,916,181
[45] Date of Patent: Jun. 29, 1999

[54] HEAD GEAR FOR DETECTING HEAD MOTION AND PROVIDING AN INDICATION OF HEAD MOVEMENT

[75] Inventors: Roger David Socci, Reston, Va.; Robert Leslie Wakenight, New Market, Md.

[73] Assignee: Creative Sports Designs, Inc., Reston, Va.

[21] Appl. No.: 08/957,073

[22] Filed: Oct. 24, 1997

[51] Int. Cl.⁶ .................................................. A61B 5/00
[52] U.S. Cl. .................................................. 600/595
[58] Field of Search .................................. 600/587, 595; 273/26 R; 33/511, 512

[56] References Cited

U.S. PATENT DOCUMENTS

| | | |
|---|---|---|
| 4,300,765 | 11/1981 | Stringham . |
| 4,326,303 | 4/1982 | Rappleyea . |
| 4,446,480 | 5/1984 | Breglia et al. . |
| 4,502,035 | 2/1985 | Obenauf et al. . |
| 4,517,417 | 5/1985 | Murayama . |
| 4,605,226 | 8/1986 | Morrissey . |
| 4,729,132 | 3/1988 | Fierro . |
| 4,826,165 | 5/1989 | Socci . |
| 4,869,509 | 9/1989 | Lee . |
| 5,003,631 | 4/1991 | Richardson . |
| 5,108,104 | 4/1992 | Johnson . |
| 5,142,700 | 8/1992 | Reed . |
| 5,221,088 | 6/1993 | McTeigue et al. . |
| 5,251,902 | 10/1993 | Federowicz et al. . |
| 5,287,562 | 2/1994 | Rush, III . |
| 5,372,365 | 12/1994 | McTeigue et al. . |
| 5,380,001 | 1/1995 | Socci et al. . |
| 5,428,846 | 7/1995 | Socci et al. . |
| 5,447,305 | 9/1995 | Socci et al. . |
| 5,524,894 | 6/1996 | Shannon . |
| 5,538,250 | 7/1996 | Putz . |
| 5,539,935 | 7/1996 | Rush, III . |
| 5,546,609 | 8/1996 | Rush, III . |
| 5,558,585 | 9/1996 | Nolan, Jr. . |
| 5,573,011 | 11/1996 | Felsing ..................................... 600/595 |
| 5,615,132 | 3/1997 | Horton et al. . |
| 5,645,077 | 7/1997 | Foxlin ..................................... 128/774 |
| 5,713,804 | 2/1998 | Socci et al. .............................. 473/422 |

FOREIGN PATENT DOCUMENTS 131040  5/1993  Japan .

OTHER PUBLICATIONS

Electronic Baseball (Babe Ruth would die); Daniel Ruby; Jul. 1982, Popular Science, p. 63.

Declaration In Support Of An IDS, by Roger Socci Jan. 1998.

*Primary Examiner*—Max Hindenburg
*Attorney, Agent, or Firm*—Hunton & Williams

[57] ABSTRACT

Apparatus and method for using head gear to sense the motion of the wearer's head and output a signal indicative of the motion. Sensors are used to detect head motion about two mutually perpendicular axes. The sensor signal is fed into a microprocessor to compute a feedback signal indicative of the deviation of the motion from a desired, preprogrammed path. The feedback signal is delivered to an indicator to alert the wearer of the head motion. The device is adaptable to monitor head motions for various athletic, sporting and safety applications.

31 Claims, 6 Drawing Sheets

HEAD GEAR FOR DETECTING HEAD MOTION AND PROVIDING AN INDICATION OF HEAD MOVEMENT

FIELD OF THE INVENTION

The present invention relates to head gear for sensing the motion of the wearer's head and providing an audible indication or other alarm signal when certain predetermined paths of head movement are detected.

BACKGROUND OF THE INVENTION

The ability to monitor the motion of a person's head has importance in many applications. For example, in many sports, the relative position and/or motion of a player's head is essential in executing a desired athletic movement. Typically, in order to achieve the correct head position or movement, the player must practice. Traditionally, such practice has encompassed repeating the position or movement until it is properly executed. A significant problem with this repetitive practice approach is the player must generally rely on self-inspection to determine whether the motion or position is correct. Endless hours of unknowingly practicing the incorrect motion will input improper data into the player's muscle memory and will make it difficult for the player to achieve the intended improvement. A second party observer (e.g., a coach) can sometimes provide insight to correct the motion. However, this method depends upon the knowledge, communication skills and availability of such an expert observer. A video tape recorder can substitute for an observer. However, using a video recording requires the purchase of costly equipment and often the tape can only be viewed after the practice session has taken place. Thus, corrections can only be attempted at a subsequent practice session.

Monitoring head movement and relative position has numerous safety applications. For example, in those sports considered to be contact sports (e.g., football, hockey, lacrosse, etc.), a player making contact with his or her head in the wrong position risks injury. A warning signal would give the player an opportunity to alter his or her head position in time to avoid injury. Current head gear for these types of contact sports do not provide any sensor information to indicate a dangerous head position.

A head position monitor has safety applications in situations where head position indicates other dangerous conditions. For example, certain movements of an automobile driver's head indicate that the driver has fallen asleep at the wheel or is not looking at the road. Many accidents could be avoided if the driver is prompted to regain proper head position. Likewise, in aviation a pilot's head position in certain instances can create a potentially dangerous situation. For example, when an aircraft is in a turn and a pilot's head is positioned at an improper angle with respect to the vertical of the centerline of the aircraft, disorientation can occur. This may occur when the inner ear of a pilot provides an erroneous sense of turn information to the pilot while making a prolonged, constant bank turn such that the pilot may incorrectly believe that he or she has ceased turning and has leveled off. While many cockpits include attitude and altitude indicators to alert the pilot to the aircraft's attitude and altitude, current head gear for pilots do not provide a head position sensor indicating a dangerous, prolonged, constant banked turn. Providing an alarm alerting the pilot of improper head position can be a significant safety advantage in this circumstance.

Many drawbacks exist among current head position monitors. For example, many devices are not sensitive to small amplitude head motions, thus, these motions remain undetected. Another drawback of existing devices is that often the desired motion requires a deliberate, predetermined head motion and many existing devices are set to merely indicate when the head has moved. For example, to properly hit a baseball the batter's head should move to follow the pitch from the pitcher to the catcher. Existing head motion sensors that merely indicate when a batter's head moves are not useful to indicate the proper head motion to the batter. Another drawback is that many existing devices are bulky and cumbersome. To be practical, a head motion monitor should interfere with the wearer and activity as little as possible. Another drawback is that many existing devices are not adaptable to the skill level of the wearer. For example, the acceptable range of head motion for a professional baseball batter is smaller than the acceptable range of head motion for a little league baseball batter and many existing devices cannot adapt to these different ranges.

These and other drawbacks exist in current devices.

SUMMARY OF THE INVENTION

An object of the invention is to overcome the above enumerated drawbacks and others present in existing devices.

Another object of the invention is to provide head gear that provides real time feedback to the wearer to aid the wearer in maintaining proper relative head position while participating in sports.

Another object of the invention is to provide head gear that detects the motion of the wearer's head about two mutually perpendicular axes.

Another object of the invention is to provide a very simple device to teach players the correct method for hitting a ball.

Another object of the invention is to provide head gear that relays safety information to the wearer regarding the wearer's head position.

Another object of the invention is to provide head gear with memory capable of storing data pertaining to desired motions.

Another object of the invention is to provide real time feedback to the wearer to aid the wearer in achieving proper head motion and related shoulder position during the course of a swing while participating in sports.

Another object of the invention is to provide real time feedback to pilots during a turn indicating a dangerous, prolonged, constant banked turn.

Another object of the invention is to provide head gear capable of alerting a driver of a potentially dangerous head position.

To accomplish these and other objects of the invention there is disclosed head gear to be worn when it is desirable to have an indication of the wearer's head motion or position. The head gear may be incorporated into an existing article of head wear. The incorporation may be permanent, or the head gear may be alternatively attached to various articles of head wear. Integral with the head gear are motion and/or position sensing devices to indicate the motion or position of the wearer's head. The data from the sensors may be fed into a digital processor to process the sensed data and derive a signal indicative of the wearer's head motion or position. Some embodiments employ a programmable processor to adapt the head gear to a variety of applications. The signal indicative of head motion or position may be fed into an indicator to provide the wearer with a recognizable feedback signal indicative of head motion or position.

Preferably, the head gear comprises a unitary construction that can be incorporated into existing head wear. The head gear is preferably of such a size and weight to be relatively unobtrusive to the wearer. Some embodiments of the head gear are attachable to more than one kind of existing head wear to enable use in multiple applications. Some embodiments of the head gear may be permanently incorporated into existing head wear.

Among other applications, the head gear allows the wearer to practice and perfect a desired motion. For example, applied to baseball, the head gear provides the wearer with feedback indicating the amount of head tilt and head rotation that occurs during the act of swinging a bat at a pitch. The batter receives feedback during the swing, allowing the batter to immediately pinpoint the correct or incorrect head motion. Thus, the batter is provided with the information necessary to correct his or her head position for the next swing and does not have to rely on guess work. The batter receives the information instantaneously, he or she does not have to wait to view a video later, or after the practice session has ended. Furthermore, there is no need to acquire and rely on a second party observer. The head gear allows the wearer a simple and relatively inexpensive method and apparatus to practice.

When the head motion monitor is used in safety applications the operation is similar. The motion and/or position sensing devices indicate the motion or position of the wearer's head. The data from the sensors are fed into a processor to process the data and derive a signal indicative of the wearer's head motion or position. The processor is programmed to indicate when the wearer's head is in an unsafe position and to output a signal to the indicator to notify the wearer of the unsafe condition. Thus, the head gear can be used to help reduce the risk of injury in many situations.

DETAILED DESCRIPTION OF THE PREFERRED EMBODIMENTS

Figure 1:
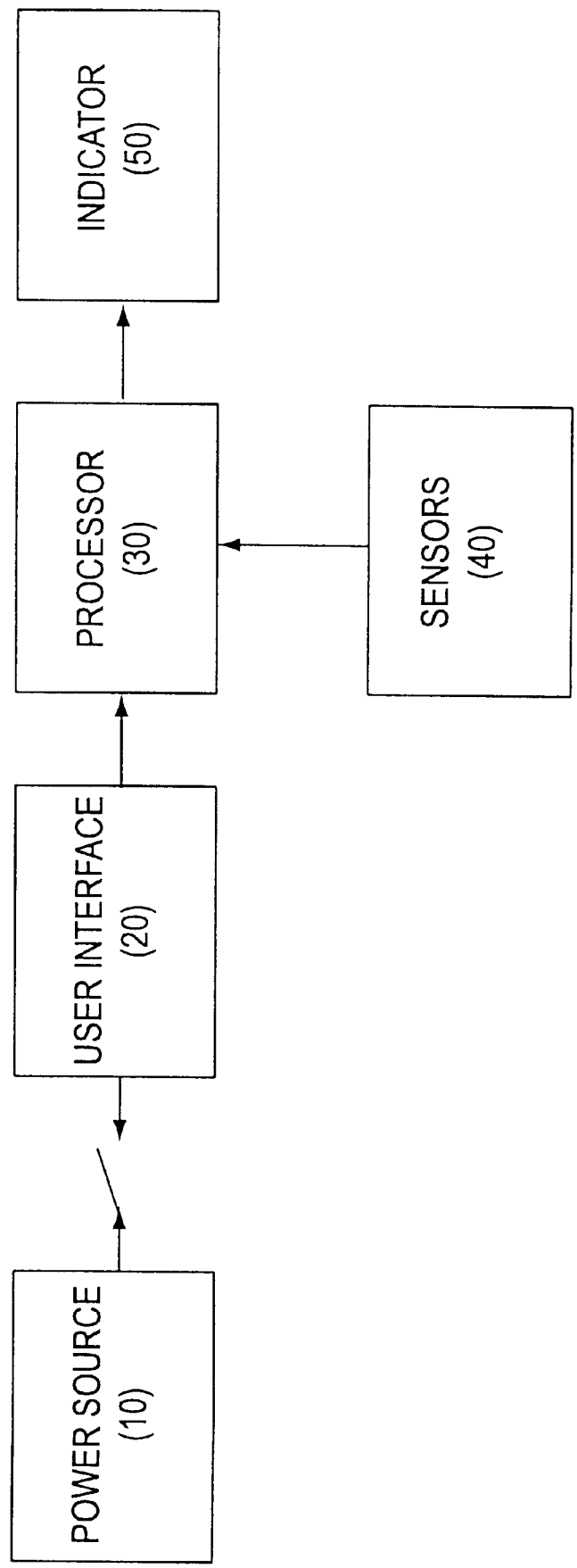
FIG. 1 is a schematic block diagram of an embodiment of the present invention.

The operation of the present invention to achieve the objects stated above will be better understood by reference to the drawings and detailed description below.

The head motion sensor head gear apparatus, to achieve the objects of the invention, may include five main functional blocks: power supply, processor, sensing mechanism, user interface, and an indicator. These functional elements operate to provide the benefits described above. Each block is discussed separately below. However, they operate together as indicated.

Power Supply

The power source 10 for the head gear preferably comprises a standard 9 Volt alkaline battery. These batteries are readily available in the retail market and are inexpensive. The 9 Volt battery has sufficient capacity to power the head gear for approximately 30 hours of continuous operation. More exotic batteries (e.g., Ni-Cad, etc.,), renewable batteries, rechargeable batteries or other suitable power sources are available. Other embodiments, having different power requirements may employ other power sources. For example, power sources supplying more or less than 9 V may be incorporated as desired.

Preferably, the 9 Volts from the battery may be regulated to the required 5 Volts by a linear voltage regulator. A protection device, such as a blocking diode, may be used to protect the regulator if the battery is inadvertently installed with the wrong polarity. A momentary switch can be used as the power on/off switch. This switch and associated circuitry apply power to processor 30 for a long enough time for processor 30 to "wake up" and latch the on condition of the head gear. In one embodiment, the head gear can be turned off in two different ways. First, the user can activate the momentary power switch to turn the head gear on or off. Second, the processor 30 can turn off the head gear on its own. For example, if the processor 30 has determined that the head gear has not been used for a preprogrammed period of time, the processor 30 will unlatch the power source 10 and go to "sleep." This feature conserves the available power source 10 capacity in those applications where power conservation is desirable.

Processor

Processor 30 is preferably a microprocessor chip, for example, the Microchip PIC16C72 or PIC16C73. This type of processor typically has 2–4K bytes of on-chip program memory, 128– 192 bytes of on-chip data memory, 3 timer modules, 5 analog to digital converter channels (8 bit resolution), a watchdog timer, power on reset circuitry, programmable I/O pins, and interrupt capabilities. These values are merely exemplary of the features desirable to provide a single chip solution to the processing requirements. The PIC16C73 also comprises a universal asynchronous receiver/transmitter (UART) to enable interfacing with a personal computer (or the like). This capability is advantageous for those embodiments where it is desired to perform data analysis or other diagnostics. Processor 30 may also comprise similar microprocessors chips made by other manufacturers.

The power on reset circuitry ensures that the processor is properly initialized when first turned on. The watchdog timer ensures that the program embedded in the processor is running properly. If the program should "crash," that is cease to function properly, the processor will automatically reset itself. For those embodiments of the head gear comprising two motion sensors, preferably, two channels of the analog to digital converter are used to convert the analog data from the two sensors into a digital form which can be analyzed by the embedded program in the processor. Preferably, two of the available timer modules are used in the head gear. One timer is, preferably, set to interrupt at a 60 Hz rate. This is the sample period for the analog to digital conversions and also provides a timer tick for various time-out periods in the operation of the head gear. The second timer is, preferably, programmed to interrupt on every half cycle of the selected frequency being applied to the indicator. Preferably, programmable I/O pins are used to read the user interface switches, to provide drive for the audible indicator, and to control the power supply latching circuitry.

For embodiments of the head gear equipped with the ability to store data in memory additional processor chips may be provided. For example, a static RAM chip may be incorporated into the head gear to enable the ability to store sensor data. Typically, the static RAM may operate with a processor such as an Intel 80C51 processor, or a similar device. Such a processor may be used instead of the above described PIC type microprocessor. A flash memory device may also be incorporated into embodiments where the speed of data storage is not an issue. Other types of memory storage chips may also be used.

Sensors

In some embodiments, the head gear preferably uses two sensors 40 and measures the angular motion of the wearer's head about two axes. One sensitive axis passes through the ears of the wearer and will be referred to as the X axis. The second sensitive axis passes out the top of the wearer's head and will be referred to as the Z axis. Other embodiments may comprise more sensors to detect motion about other axes. For example, sensors may be incorporated to detect motion along the Y axis, which can be envisioned as passing horizontally out through the tip of the wearer's nose. For embodiments where motion detection is only along one axis, fewer sensors may be used.

Rotation about the X axis is a measure of the tilt of the wearer's head. In those embodiments of the head gear adapted to sports, it is important to monitor head tilt because, in many sports the degree and direction of a player's head tilt is indicative of the correctness of the motion. For example, in baseball, a batter's head should not tilt up during the swing and, in fact, should naturally tilt slightly downward. Likewise, in golf a player's head should not tilt up during a swing. Therefore, if the tilt of the head is up, the player is not watching the ball to the point at which the bat or club contacts the ball.

Rotation about the Z axis is a measure of the rotation of the wearer's head during the motion. For example, in many sports it is preferable for the player's head to follow the motion of the ball throughout the swing. For example, in baseball, a batter's head should initially rotate slightly, from the set position of the stance, toward the catcher. This indicates that the batter is actually tracking the baseball as it leaves the pitcher's hand and approaches home plate. The batter's head should stay in this position until some time after the baseball is contacted. Training the head to remain in position until some time after contact helps to ensure that the batter is getting proper separation of the head from the front shoulder during the swing. If the rotation of the batter's head is initially away from the catcher, the batter is not tracking the ball properly and is said to be "pulling off the ball." If the rotation away from the catcher occurs too quickly, the batter will not be getting the proper separation of head and front shoulder during the swing and the batter will not contact the ball properly. Similar head rotation analysis for other sports can also be accommodated by the head gear.

One embodiment of the head gear measures the angular motion around the two sensitive axes (e.g., X and Z) with two gyroscopes oriented such that each gyroscope is only sensitive to rotations about one of the axes. The outputs of the gyroscopes are, preferably, analog voltages proportional to the angular rate at which the gyroscope is moving about its axis of sensitivity. The gyroscopes are preferably mounted on head gear being worn by the player, therefore, the outputs of the gyroscopes are indicative of the angular motion of the wearer's head about the two sensitive axes. The data output of the gyroscopes is proportional to the speed of rotation and a simple mathematical manipulation of the data yields the position of the wearer's head. A single integration of speed data yields the distance traveled relative to a starting point. Thus, the motion and position of the wearer's head can be monitored by the sensors. In one embodiment the gyroscopes can be Murata part number ENC-05E gyroscopes giving an output in millivolts per degrees per seconds. Other gyroscopes can also be used.

Alternative embodiments may use a different sensor configuration. For example, a combination of gyroscopes and accelerometers may be used to enable monitoring the wearer's head position. Other position and motion sensors may be used.

User Interface

The head gear may enable the user to input information into the processor. Preferably, data entry can be accomplished through a user interface 20. One example of data input is whether the user wants the head gear activated. Preferably, a power on/off selector is provided in the user interface for this purpose. Another example of user data entry applies to embodiments adapted for sports training. The user may input the particular sport or application that the head gear is being used to monitor. For example, the user can input a "baseball" selection when the user desires to practice a baseball batting swing. After selecting the particular application, further information may be inputted into the head gear. For example, head gear adapted for use as a baseball batting trainer requires the user to input whether the user is left or right handed. This allows the processor to determine the preferred direction of head rotation. For example, rotations about the Z axis towards the catcher are "good" because, they indicate proper tracking of the motion of the ball towards the batter. Similarly, rotations about the Z axis away from the catcher are "bad". However, for a right-handed batter "good" rotations are clockwise, "bad" rotations are counter-clockwise. The situation is reversed for a left-handed batter. Thus, in this embodiment, the processor must know which situation exists in order to properly interpret the rotation data. In one embodiment the on/off switch is a dual function switch, controlling both the power and the right/left-handed selections. Other embodiments may have separate right/left and on/off switches.

Other user inputs to the head gear are possible. For example, the user could control such things as the volume level of an audible indicator, activating a save data setting or set up the head gear to judge head motion based on the skill level of the head gear user (e.g., novice or expert).

Indicator

Some embodiments comprise indicator 50 which provides both positive and negative feedback to the user of the head gear. The indicator 50 may provide, for example, audible signals to the wearer. In these embodiments the indicator 50 is, preferably, a piezo ceramic speaker. Drive to the speaker can be provided by one (or more) of the programmable I/O pins of the processor. The speaker is preferably driven by a square wave, the duration and frequency of which is controlled by the processor 30. Other drivers or signal indicators are possible. For example, synthesized or recorded speech may be incorporated into the indicator. Visible indicator signals, for example LED's or the like, are also possible.

The exact frequencies, duration, or the combinations of on and off times provided to the user are not important. The only requirement is that the user is able to readily differentiate between the various indications, in order to clearly discern the information being provided.

Some embodiments of the head gear employ several different audible indications. A "greeting" sequence may be sent when the head gear is turned on. If necessary, the user may make the various data inputs that may be desired (e.g., right/left-handed batter selection) during the greeting tone.

In some embodiments, an "armed" or "ready" indicator may be sent when the head gear has determined that the wearer is at rest and presumably has adopted the set or stance position in preparation to beginning the desired motion. The importance of establishing a wearer's starting position will be explained in the algorithm section below. The wearer waits for the "armed" indication before and between motions, to allow the head gear to properly monitor the motion.

In some embodiments, a "good" indicator, indicating proper head motion, can be sent during the monitored motion, and the actual indication being sent can be proportional to the degree of motion (e.g., as the degree of motion increases, the frequency of an audible tone increases or the frequency of a flashing LED increases). Alternative embodiments of the head gear may use a single fixed frequency audible indicator for "good" with the degree of "good" being indicated by a varying intensity sound instead of a varying frequency sound. The same may be applied to a visible indicator with an increase in visual signal intensity proportional to the degree of motion.

For some embodiments, a distinctive "bad" indicator may be sent when the head gear has determined that excessive "bad" or out of range motion has occurred. The "bad" indicator may interrupt any "good" indicator in progress, to indicate an improper head motion has occurred.

In some embodiments, silence, or no indicator, can be used to indicate either "good" or "bad" head motion depending upon the desires of the user.

Algorithm

For those embodiments sensing motion along two axes, preferably, the analysis of the head motion may be based upon the integration of the raw data collected from two sensors. These sensors are preferably two gyroscopes, one sensitive to motion about the X axis (i.e., head tilt) and one sensitive to motion about the Z axis (i.e., head rotation). As mentioned previously, the outputs of the gyroscopes may be proportional to angular speed of rotation so a single integration will yield distance traveled about an axis in degrees. For embodiments sensing motion along a different number of axes, the algorithm is similar, however, the number of sensors may vary.

An important point to consider is that, in some embodiments, this integration can be, preferably, deliberately imprecise. In these embodiments, the actual integrator is a "leaky" integrator. A small portion of the accumulated integration may be discarded after every update. This prevents small errors due to noise or a small error in the initial reference for the integration from being accumulated. The actual arithmetic is also not precise. A more exact numerical integration would require multiplication. A precise integration would require floating point rather than fixed point arithmetic. These both cost processor time. The analog to digital conversion is, preferably, limited to 8 bits of resolution. The actual sensor output can be subject to drift with temperature and time. All these factors can eventually result in a large error in the apparent position of the head, which can be further compounded over time. In these embodiments, the apparent position of the head will only be accurate for a short period of time, thus, the desire to "arm" the head gear before every practice motion. "Arming" the head gear means having the wearer assume a stance and remain still until that fact is recognized by the head gear. The armed indicator indicates to the wearer that the integrations have reset and restarted and the head gear has refreshed the position of the wearer's head and is ready for the start of the next practice motion.

Some embodiments of the head gear can be programmed to "remember" or store the sensor readings for a particular motion. Subsequent motions can be compared to the stored data. These embodiments may require additional processor memory capabilities as noted above. For example, in a baseball batting aid embodiment, the processor can store in memory the sensor data values that occur during a chosen swing. Subsequent swings can then be compared with the stored data as a training aid. The processor can automatically store a successful motion (e.g., by selecting an "auto-store" mode) or a successful motion can be selected, by the user, after the motion has been completed. For example, in the baseball training embodiment, a player might have completed a correct swing (e.g., satisfactory contact with the ball); the player can now select the "store" mode and the sensor data for the successful swing will be stored in the processor for comparison with subsequent swings. Alternatively, the user can select an "auto-store" mode where a correct swing is automatically stored in memory.

Figure 2:
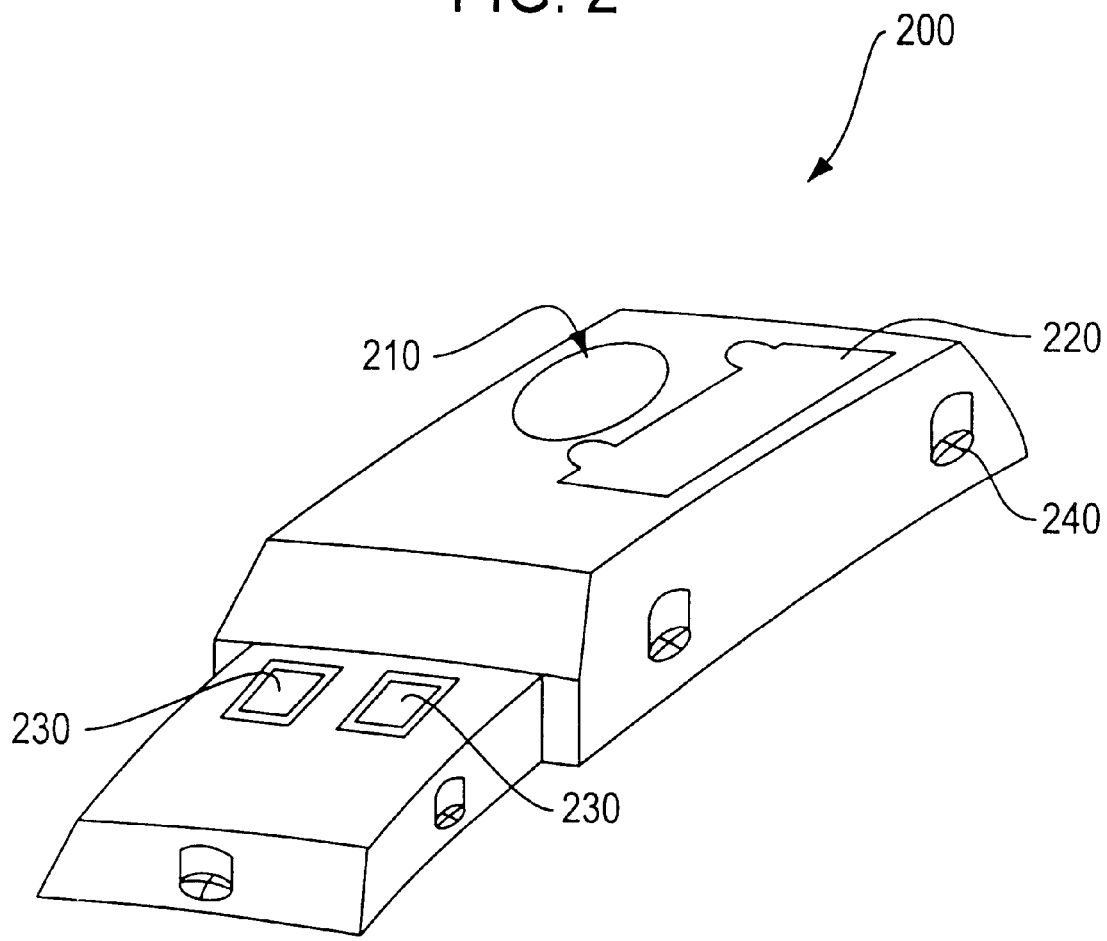
FIG. 2 is a schematic illustration of an attachable embodiment of the invention.

As shown in FIG. 2, the head gear may comprise a unitary construction. Contained within the head gear 200 are the components described above. The embodiment in FIG. 2, comprises an audible indicator, shown as a speaker element 210. A compartment 220 is provided to house a battery or similar power source. Switches 230 comprise the user interface portion. In the depicted embodiment two switches are shown, one for on/off and volume the other for left/right handed input. Other configurations of the user interface portion are possible. The head gear 200 may be attached to a suitable item of head wear prior to use. The attachment of head gear 200 may be carried out in any suitable fashion that does not significantly interfere with the wearer's performance. For example, fastening screws 240 are shown in FIG. 2 to enable attachment.

Figure 3:
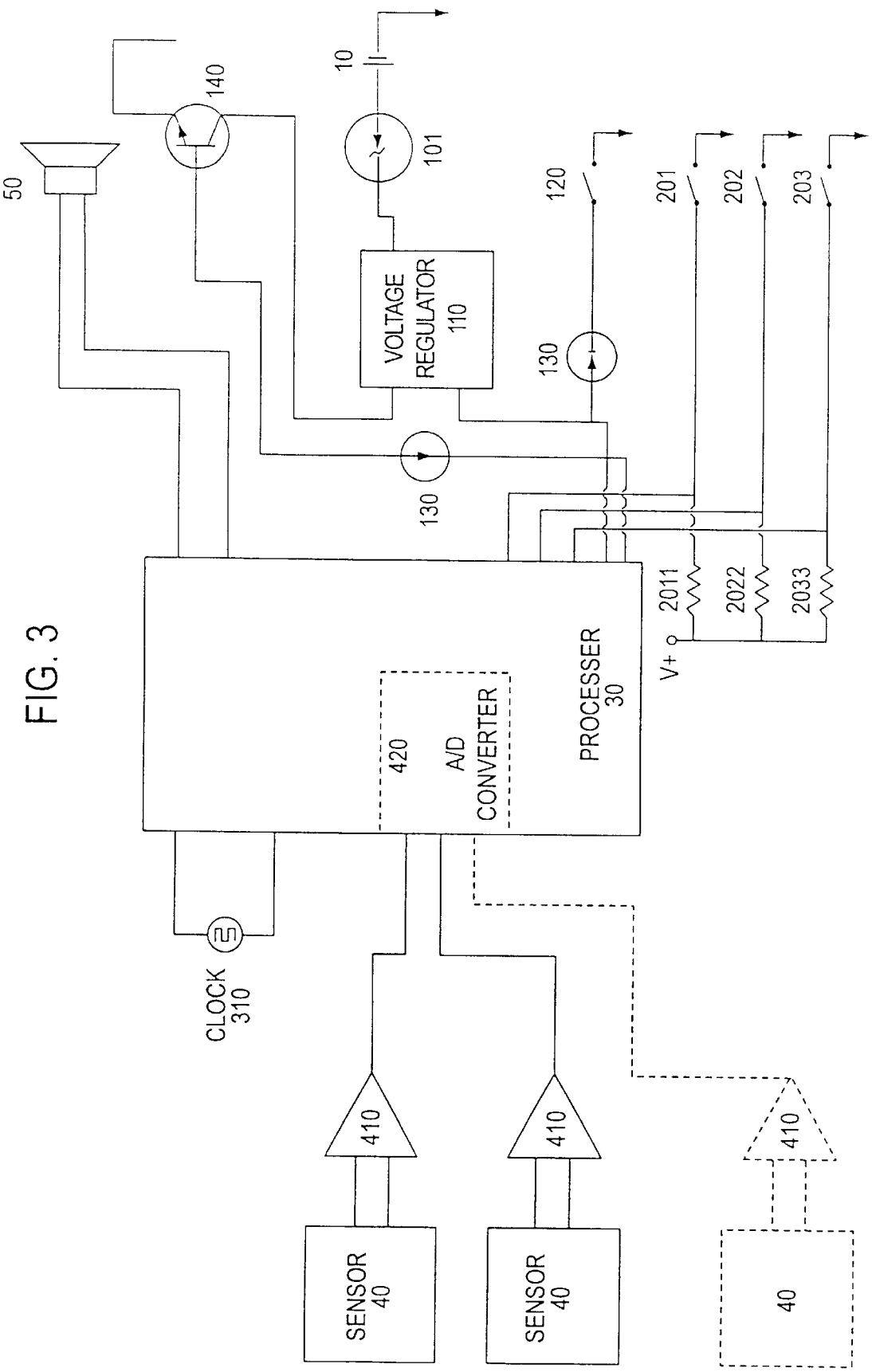
FIG. 3 is a schematic of the circuit for an embodiment of the invention.

A schematic diagram of one embodiment of the head gear is shown in FIG. 3. The number of sensors 40 used may vary according to head gear's intended application. The variability of the number of sensors is indicated in FIG. 3 by the sensor 40 shown in broken lines. The analog output of each sensor 40 may be amplified by an amplifier 410. The amplified sensor output may then serve as the input for an analog to digital (A/D) converter 420. For embodiments comprising a PIC type processor 30, the A/D converter 420 may be an integral portion of the processor chip. Clock 310 may also comprise an integral portion of the processor 30. Clock 310 provides a timer for the various time-out periods in the operation of the head gear. Indicator 50 is coupled to the output of processor 30. In FIG. 3, indicator 50 is represented schematically as an audible speaker. Other indicators, for example, a visible LED indicator, are also possible. Power for the head gear is supplied by power source 10, indicated as a battery in FIG. 3. Voltage from the power source 10 may be regulated by a voltage regulator 110. A protection device, for example, diode 101, may be used to protect the voltage regulator if power source 10 is inadvertently installed with the wrong polarity. Power on/off switch 120 may be provided to allow the user to turn the head gear on or off. Additional circuit devices, for example, diodes 130 and transistor 140, may be provided to enable a safe and effective supply of power to the head gear. In FIG. 3, the user interface is depicted as comprising switch elements 201, 202, 203. The switch elements 201, 202 and 203 are used for selecting a voltage level, determined by associated resistive elements 2011, 2022 and 2033. This voltage level may serve as input to the programmable I/O pins on the processor. In this manner, the processor can be programmed to enable the various functionalities described herein. The switch elements 201, 202 and 203 are represented as single position switches, but may comprise multiple position switches or other appropriate devices. The switches may be set to input certain values into processor 30. Other data input devices may be used, and the user interface may comprise more or less than three elements.

Sample Embodiments

The head gear described above can be adapted to perform as a head motion monitor for many applications. The following examples are included to illustrate some of the possible embodiments that the head gear can be programmed to monitor. Other embodiments will be apparent to those skilled in the art.

Baseball Training Aid

The head gear has application as a training aid in the sport of baseball. Preferably, this embodiment senses motion along the X and Z axes. The head gear can be programmed to monitor proper head motion as it pertains to the sport of baseball. For example, proper head motion is critical to good batting technique. The operation of the monitoring algorithm is, preferably, as follows. The arming algorithm looks for a small integration about both of the sensitive axes (e.g., X and Z). If the small integration persists for a programmed period of time, the batter is moving his or her head only very slightly. The head gear assumes that the batter has taken a stance and is ready for the next swing. The head gear is then "armed." While armed, the head gear constantly checks the value of the integrations about both of the sensitive axes (X and Z). Motion is deemed to have occurred if the value of the integration exceeds a programmed threshold about either axis. If a large "bad" rotation occurs before any downward tilt of the head occurs, the head gear concludes that the swing is incorrect and may send the "bad" indicator. If a downward tilt of the head occurs first, two things happen. The "good" indicator may be sent to the batter. The indication sent to the batter will be proportional to the degree of downward tilt and as the downward tilt increases the indication will change in either frequency or intensity to indicate to the player the degree of tilt. Recognition of the downward tilt may also start a timer. The period of the timer is programmable. The head gear looks for "bad" rotation during the time-out period. If "bad" rotation exceeds a programmable threshold before the timer expires, the "good" indication may be replaced by the "bad" indication. The head gear has determined that the batter's head has followed the front shoulder out, not allowing for the proper head/front shoulder separation during the swing. In particular, younger players have a tendency to look up too quickly to see where the ball has been hit. Looking up too quickly decreases the chances of achieving proper shoulder transfer during a swing. Some embodiments of the head gear may be programmed to include a long time-out period to help achieve proper shoulder transfer. When the timer expires, the head gear stops checking for rotation. This is to eliminate faulty bad indications from occurring due to motion of the head after the swing has been completed. Any rotation after this time is assumed to be after proper contact has been made with the ball, and the rotation is the result of the batter starting to track the hit ball (e.g., to determine where it lands). The sequence now restarts with the head gear once again looking to be armed.

The head gear can be adapted for use as a baseball fielding trainer. The proper technique for fielding a ground ball is for the player to keep his or her head down, watching the ball until it is secured in the player's mitt. Only after the ball is secured should the player look up to the place where the ball is to be thrown. Inexperienced players have a tendency to look up before the ball is secured. This often results in an "error" or missing the ball. The head gear can be programmed to signal the fielder to keep his or her head down until the ball is secured. The fielding embodiment may comprise a simplified design as head motion need only be detected along one axis (e.g., the X axis). Sensing along more then one axis may also be included in a fielding embodiment of the head gear.

The head gear can also be adapted to train cricket batters to maintain proper head position. As the motion of batting a cricket ball is similar to batting a baseball, the program to monitor the head motion is also similar.

Figure 4:
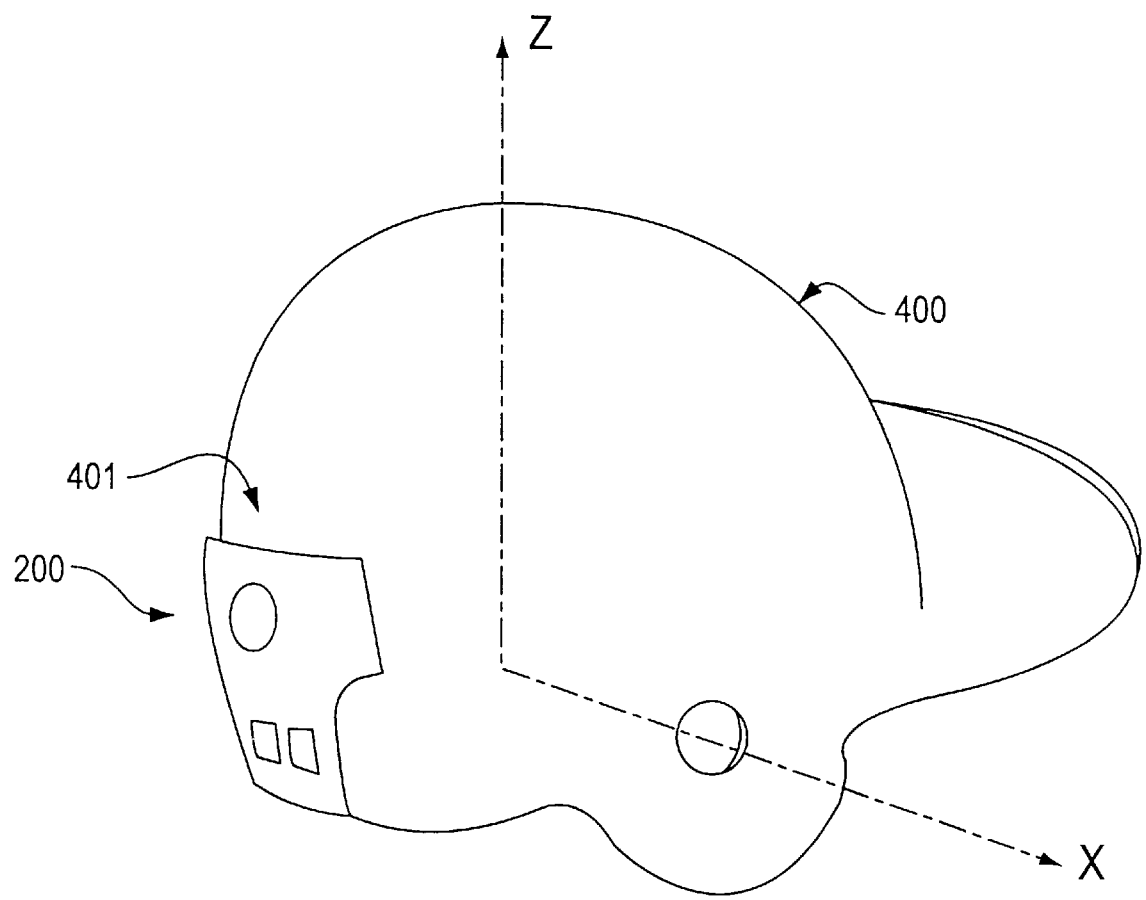
FIG. 4 depicts an embodiment of the invention as applied to the sport of baseball.

As shown in FIG. 4, the head gear 200 is attachable to an ordinary baseball batting helmet 400. The head gear may be mounted at the rear of the helmet 401 and interferes as little as possible with the normal use of the helmet. Alternatively, the head gear may be integrally formed into the batting helmet.

Hockey Training and Safety Aid

The head gear can also be adapted for use as a training aid for hockey players. Numerous actions occur in a hockey game that require the player to have proper head motion or position. Algorithms to monitor these heads motions can be programmed into the head gear, so that the motion can be practiced. For example, during a "face off" a player should keep his or her head down to watch the puck as it is dropped to the ice. If the player does not keep his or her head down, the head gear's indicators will alert the player that the head position is improper. In addition to practicing a face off, the head gear can be used to practice other activities that arise in the course of a hockey game. For example, a few situations that can be practiced using the head gear are: when tending goal a goalie's head should be down to watch the approaching puck, when a player is preparing to receive a pass the head should be down to watch the pass and control the puck with the stick (or skate), when shooting the puck a player should have the head down to watch the puck throughout the shot, when coming out of a quick turn while skating a player should have the head up, and when looking to pass the puck the head should be up. Some of these applications may be incorporated into an embodiment of the head gear that senses motion along one axis.

The head gear can be incorporated into a hockey player's safety equipment. As shown, generally in FIG. 5, the head gear 200 is adaptable to fit inside a normal hockey helmet 500 and, thus, offers the usual head protection of the normal hockey helmet. The head gear 200 may be fitted into the helmet 500 in between protective padding elements 510. Alternatively, the head gear 200 may be mounted on the outside of the hockey helmet in a fashion similar to the baseball embodiment as shown in FIG. 4. The head gear can be programmed to warn the player when his or her head is in a potentially dangerous position. In these embodiments more sensors may be included to detect motion along all three axes (e.g., X, Y and Z). For example, a player may risk neck and spine injuries by getting hit or "checked" with his or her head in the wrong position. The head gear will warn the player in advance that the head is in a potentially dangerous position and give the player a chance to correct the position.

The head gear can also be adapted to other sports similar to hockey. For example, the head gear can be programmed to provide training or safety information to participants of similar sports such as field hockey, lacrosse and soccer.

Tennis Trainer

The head gear can be adapted to provide training for certain movements in tennis. For example, the head gear can be programmed to help a player practice a tennis serve. When serving, initially the head should be up looking at the ball as it is tossed into the air. The head should remain up until the racket has contacted the ball and then the head should be looking down after contact with the ball. The head gear can also be programmed to practice the forehand and backhand strokes. During these motions the players head should be looking down at the ball and the point of contact with the racket. The head gear is programmed to give the player an indication of proper head position.

Figure 6:
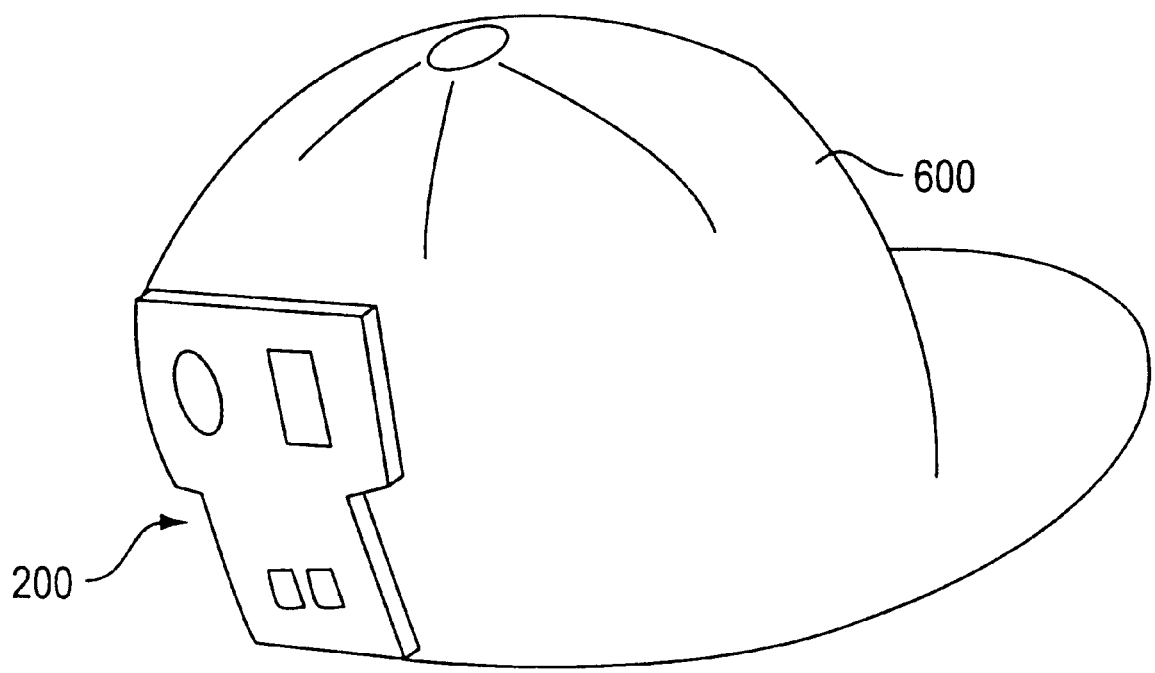
FIG. 6 depicts an embodiment of the invention attached to a cap or hat.

For this type of application, where a helmet is not normally worn, the head gear may be attached to a cap, hat, head band or other similar device to be worn while utilizing the head gear. Such a mounting is represented in FIG. 6. The head gear 200 may be attached to a cap or hat, for example, cap 600.

Football Training and Safety Aid

The head gear is adaptable to provide training for certain motions that occur in the sport of football. For example, punting and place kicking require that the player keep his or her eyes on the ball and head down during the kick. The head gear is programmed to indicate when this head position is or is not achieved.

The head gear can also be programmed to train proper blocking or tackling position. Proper form is with the player's head up and eyes open. For inexperienced players the tendency is to put the head down and close the eyes as a collision is approaching. At the least, this can cause a missed block or tackle; at worst, injuries can result. The head gear is programmed to give the player an indication of whether the head is up. When the head is properly up, the tendency is for the eyes to be open as well.

The head gear is incorporated into the same type of helmet as existing football helmets and offers the usual level of protection to the wearer. The head gear offers an additional level of protection to the wearer by alerting the wearer of improper head position. By notifying the wearer that his or her head is in a potentially dangerous position, the player can act to correct the situation and, thereby, avoid injury.

Figure 5:
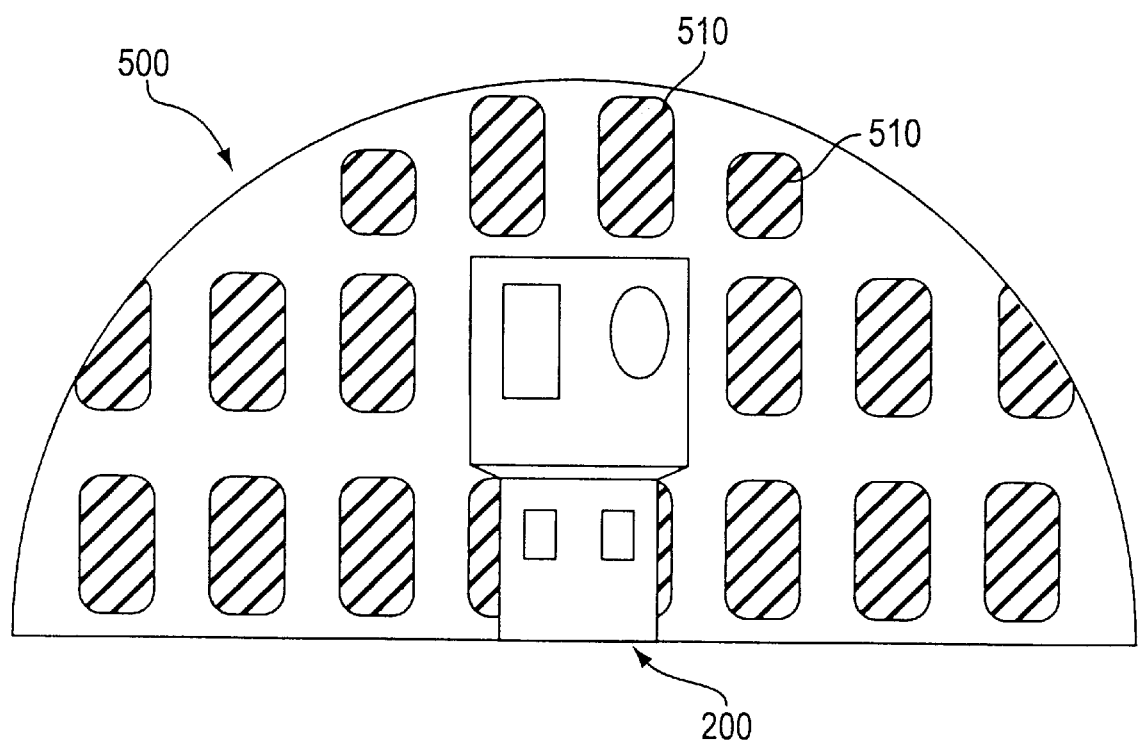
FIG. 5 depicts a partial cut-away view of an embodiment of the invention mounted within a protective helmet.

Mounting the head gear 200 inside an existing football helmet 500 is depicted schematically in FIG. 5. The head gear 200 may be mounted in between protective padding elements 510 inside the helmet so as to not interfere with the normal use of the helmet. Alternatively, the head gear may be mounted on the outside of the helmet in a manner similar to the baseball embodiment shown in FIG. 4.

Golf Swing Trainer

The head gear is adaptable to provide training for improving a golfer's swing. Throughout a swing, a golfer's head must remain as still as possible, with his or her eyes focused on the ball and the point of contact. During the top most part of the back swing the golfer's chin should be in line with his or her front shoulder. If the head remains in proper position, the golfer's chin will end up in line with his or her rear shoulder during the follow through portion of the swing. The head gear is programmed to indicate if this motion is carried out properly or not. For this embodiment the head gear is programmed to give an indication of movement of the head in any direction. Appropriate sensors may be incorporated to sense motion in any direction. The sensitivity of the detectors may be adjustable according to, among other things, the skill level of the user.

For this type of application, where a helmet is not normally worn, the head gear may be attached to a cap, hat, head band or other similar device to be worn while utilizing the head gear. Such a mounting is represented in FIG. 6. The head gear 200 may be attached to a cap or hat, for example, cap 600.

Skating Trainer and Safety Aid

The head gear is adaptable to provide training to improve skating ability. When learning to ice skate, roller skate or roller blade inexperienced skaters tend to put their heads down and look at their feet. This makes learning to skate harder because, it is difficult to maintain proper balance when looking at the feet. Keeping the head down also narrows the skater's field of vision. The narrow visual field adds to the danger of skating into an obstacle. The head gear is programmable to alert the skater to maintain upright head position. The head gear can be enclosed in a protective helmet (for example, as in FIG. 5) to offer the skater an additional level of protection.

Boxing Training Aid

The head gear is adaptable to train a boxer to keep the proper head position. Boxers should keep their heads and chins tucked down when fighting. Doing so minimizes the impact of punches landing on the boxer's face, a desirable result. The head gear can be incorporated into the normal boxing head gear and programmed to alert the boxer when his or her head comes out of the proper position. For example, if the head tilts too far up (e.g., along the X axis) an indication may be given to the fighter.

Bowling Trainer

The head gear is adaptable to indicate proper head position to a bowler. A bowler's head must be still and slightly tilted downward through the approach to the starting (foul) line, through the delivery of the ball and through the follow through motion. The head gear is programmed to indicate whether a bowler has performed the correct head motion.

For this type of application, where a helmet is not normally worn, the head gear may be attached to a cap, hat, head band or other similar device to be worn while utilizing the head gear. Such a mounting is represented in FIG. 6. The head gear 200 may be attached to a cap or hat, for example, cap 600.

Billiards or Pool Training Aid

The head gear is adaptable to aid a billiards or pool player in maintaining proper head position. When executing a proper pool shot the player's head should point slightly down and remain relatively still. The head gear is programmed to indicate when this proper position is maintained.

For this type of application, where a helmet is not normally worn, the head gear may be attached to a cap, hat, head band or other similar device to be worn while utilizing the head gear. Such a mounting is represented in FIG. 6. The head gear 200 may be attached to a cap or hat, for example, cap 600.

Archery or Shooting Aid

The head gear is adaptable to be used as a training aid for archery and shooting sports. The head gear can be programmed to monitor the proper head positioning to enable successful completion of archery or shooting motions.

For this type of application, where a helmet is not normally worn, the head gear may be attached to a cap, hat, head band or other similar device to be worn while utilizing the head gear. Such a mounting is represented in FIG. 6. The head gear 200 may be attached to a cap or hat, for example, cap 600.

Driver Alertness Aid

Many automobile accidents are caused when the driver falls asleep at the wheel or when the driver is distracted and looks away from the road for too long. Another embodiment of the head gear can be programmed to alert the driver of this dangerous condition. The optimal position for an alert driver's head is upright and facing forward. Some short term "head checking" motion where the driver looks to the side, for example, to see if neighboring lanes are clear is also permissible. When a driver falls asleep, or becomes distracted, his or her head will deviate from the optimal position. Multiple sensors may be provided to detect head motion in any direction. If the sensors determine that the head has been in a non-optimal position for too long, the program will activate the indicator to alert the driver to revert to the correct position.

For this type of application, where a helmet is not normally worn, the head gear may be attached to a cap, hat, head band or other similar device to be worn while utilizing the head gear. Such a mounting is represented in FIG. 6. The head gear 200 may be attached to a cap or hat, for example, cap 600. Alternatively, the head gear may be incorporated into a protective helmet (for example, as in FIG. 5) and may offer an additional level of safety to the driver.

Pilot Alertness Aid

When an aircraft is in a turn and a pilot's head is positioned at an angle with respect to the vertical of the centerline of the aircraft, disorientation can occur. The head gear can be incorporated into a pilot's head gear to provide an alarm as to improper head position. The head gear may be programmed to act as a warning device. The pilot may be provided with a head position information only if there is prolonged consistent angle of bank turning so that the pilot is aware that although his or her sense of balance may suggest straight and level flight, the aircraft is actually still turning and descending.

Other embodiments and uses of the invention will be apparent to those skilled in the art from consideration of the specification and practice of the invention disclosed herein. For example, the head gear may be adapted to other types of athletics not specifically enumerated herein. Athletics may include activities where physical motion occurs and where the monitoring of head position may be useful. The specification and examples should be considered exemplary only. The intended scope of the invention is only limited by the claims appended hereto.

What is claimed is:

1. Head gear apparatus to sense the instantaneous position of the wearer's head relative to a desired head position for a specific physical movement and to provide a signal to the wearer when the wearer's head is within proper head position parameters for said specific physical movement, or, alternatively, to provide a signal to the wearer when the wearer's head is not within said proper head position parameters for said specific physical movement, comprising:

sensor devices sensing the movement of the wearer's head from a known initial position established at a time prior to initiation of said specific physical movement and outputting an electrical signal indicative of the direction and rotational speed of the wearer's head movement;

an analog to digital converter for converting said electrical signal to a digital data stream, a digital processor for receiving said digital data stream, performing an integration to calculate an angular displacement related to said electrical signal and comparing said calculated angular displacement to a predetermined digital datum establishing criterion limits for correct movement, said digital processor receiving further data, comprising additional information, to assist in comparing said criterion limits and said calculated angular displacement to determine whether the wearer's head is within or is not within said criterion limits;

an alarm output device for generating an alarm when a specific movement is within or not within said established criterion, and an interface device for enabling input of at least some of said additional information to said digital processor.

2. Head gear to sense, during a specific movement associated with a particular type of physical activity, the relative position of the wearer's head to an established track for said specific movement and providing an alarm when said relative position is outside said established track, and to provide another alarm when said relative position is inside said established track, comprising:

gyroscope sensors, each oriented around an axis of head rotation, and each outputting an analog electric signal proportional to angular rotation of the wearer's head about each sensed axis, an analog to digital converter for creating a digital output for each said signal, a data integrator and processor for receiving said digital outputs and creating from said digital outputs a digital signal indicative of the relative angular displacement of the wearer's head in said physical activity, said data integrator and processor comparing said digital signal to established limits for correct movement, said data integrator and processor receiving further data, comprising additional information, to assist in comparing said established limits and said digital signal to determine whether the wearer's head is within or is not within said established limits;

an alarm device for outputting a signal for alerting the wearer when said relative movement falls outside said limits and said alarm device for outputting another signal when said relative movement falls inside said limits, and an interface device for enabling input of additional information to said data integrator and processor.

3. Head gear apparatus to sense the motion of the wearer's head and to provide an indication of the character of the sensed motion comprising:

user interface means to allow the user to input information into the head gear, sensor means detecting the wearer's head motion about two mutually perpendicular axes and outputting a signal proportional to the detected motion, processor means receiving the output signal of the sensor means and calculating from the output signal at least an angular displacement, that is compared with stored data and the information input at the user interface means, manipulating the calculated angular displacement and the information input to create a feedback signal, and indicator means receiving the feedback signal and providing a recognizable indication of the feedback signal to the wearer.

4. The head gear apparatus of claim 3 wherein the feedback signal is proportional to the deviation of the wearer's head from a desired path of motion.

5. The head gear apparatus of claim 4 wherein the stored data is represented by information indicative of the desired path of motion.

6. The head gear apparatus of claim 4 wherein the desired path of motion is selected from the group of physical activities consisting of: athletics, baseball, cricket, hockey, field hockey, lacrosse, soccer, tennis, football, golf, skating, boxing, bowling, billiards, pool, archery, shooting, automobile driving and aircraft piloting.

7. The head gear of claim 3 wherein the indicator means comprises an audible sound generating means.

8. The head gear of claim 7 wherein said audible sound generating means produces an output recognizable as verbal speech.

9. The head gear of claim 3 wherein said indicator means comprises a visible signal generating means.

10. The head gear apparatus of claim 3 wherein the sensor means comprise gyroscopic sensors.

11. The head gear apparatus of claim 3 wherein the sensor means comprise a combination of gyroscopic sensors and accelerometer sensors.

12. The head gear apparatus of claim 3 wherein the processor means stores data representing the output signal of the sensor means.

13. A method detecting the motion of head gear and providing a wearer of the head gear information relating to the detected motion, the method comprising:

providing user input means to allow the wearer to input information into the head gear, providing sensing means to sense the motion of the wearer's head about two mutually perpendicular axes and output a signal proportional to the sensed motion, providing processor means to manipulate the output signal and calculate from the output signal at least an angular displacement, that is compared with stored data and the input information to create a feedback signal, and providing indicator means to receive the feedback signal and provide a recognizable indication of the head gear motion to the wearer.

14. The method of claim 13 wherein feedback signal is generated in proportion to the deviation of the wearer's head from a desired path of motion.

15. The method of claim 14 wherein the stored data is indicative of the desired path of motion.

16. The method of claim 14 wherein the desired path of motion is selected from the group of physical activities consisting of: athletics, baseball, cricket, hockey, field hockey, lacrosse, soccer, tennis, football, golf, skating, boxing, bowling, billiards, pool, archery, shooting, automobile driving and aircraft piloting.

17. The method of claim 13 wherein the indicator means generates an indication comprising an audible sound.

18. The method of claim 17 wherein the audible sound comprises an output recognizable as verbal speech.

19. The method of claim 13 wherein the indicator means generates an indication comprising a visible signal.

20. The method of claim 13 wherein the sensing means sense motion with gyroscopic sensors.

21. The method of claim 13 wherein the sensing means sense motion with a combination of gyroscopic sensors and accelerometer sensors.

22. Head gear apparatus to sense the motion of the wearer's head and to provide an indication of the character of the sensed motion comprising:

means for interfacing the head gear to enable the input of information into the head gear, means for sensing to detect the wearer's head motion and output an electrical signal proportional to the detected motion, means for converting an analog signal to a digital signal to create a digital output for each said electric signal, means for processing to receive the output signal of the means for sensing and calculate from the output signal at least an angular displacement, that is compared with stored data and any information input at the means for interfacing, and to process the output signal and any information input to create a feedback signal, and means for indicating to receive the feedback signal and provide a recognizable indication of the feedback signal to the wearer.

23. The head gear apparatus of claim 22 wherein the feedback signal is proportional to the deviation of the wearer's head from a desired path of motion.

24. The head gear apparatus of claim 23 wherein the stored data is represented by information indicative of the desired path of motion.

25. The head gear apparatus of claim 23 wherein the desired path of motion is selected from the group of physical activities consisting of: athletics, baseball, cricket, hockey, field hockey, lacrosse, soccer, tennis, football, golf, skating, boxing, bowling, billiards, pool, archery, shooting, automobile driving and aircraft piloting.

26. The head gear of claim 22 wherein the means for indicating comprises a means for generating an audible sound.

27. The head gear of claim 26 wherein said means for generating an audible sound produces an output recognizable as verbal speech.

28. The head gear of claim 22 wherein said means for indicating comprises a means for generating a visible signal.

29. The head gear apparatus of claim 22 wherein the means for sensing comprise gyroscopic sensors.

30. The head gear apparatus of claim 22 wherein the means for sensing comprise a combination of gyroscopic sensors and accelerometer sensors.

31. The head gear apparatus of claim 22 wherein the means for processing stores data representing the output signal of the means for sensing.

* * * * *